US010053248B2

(12) United States Patent
Joplin

(10) Patent No.: US 10,053,248 B2
(45) Date of Patent: Aug. 21, 2018

(54) SYSTEMS AND METHODS FOR PRESCRIPTION CONTAINER SHIPPING

(71) Applicant: Express Scripts, Inc., St. Louis, MO (US)

(72) Inventor: Jonathan W. Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 354 days.

(21) Appl. No.: 14/887,730

(22) Filed: Oct. 20, 2015

(65) Prior Publication Data

US 2017/0107005 A1    Apr. 20, 2017

(51) Int. Cl.
*B65B 35/26* (2006.01)
*B65B 35/56* (2006.01)

(52) U.S. Cl.
CPC ........... *B65B 35/26* (2013.01); *B65B 35/56* (2013.01)

(58) Field of Classification Search
CPC ........ B65B 35/26; B65B 35/56; B65B 35/10; B65B 35/58; B65B 37/00; B65B 37/08; B65B 57/00; B65B 57/06
See application file for complete search history.

(56) References Cited

U.S. PATENT DOCUMENTS

| | | | |
|---|---|---|---|
| 3,653,176 A * | 4/1972 | Gess | B65B 43/50 156/384 |
| 5,713,485 A * | 2/1998 | Liff | G06F 19/3462 221/2 |
| 5,771,657 A | 6/1998 | Lasher et al. | |
| 6,769,228 B1 | 8/2004 | Mahar | |
| 6,892,512 B2 | 5/2005 | Rice et al. | |
| 7,010,899 B2 | 3/2006 | McErlean et al. | |
| 7,412,814 B2 * | 8/2008 | Rice | B65B 5/103 53/494 |
| 8,215,540 B2 * | 7/2012 | Szesko | G06F 19/3462 235/375 |
| 8,731,711 B1 | 5/2014 | Joplin et al. | |
| 9,878,812 B2 * | 1/2018 | Ford | B65B 21/242 |

* cited by examiner

*Primary Examiner* — David Walczak
(74) *Attorney, Agent, or Firm* — Husch Blackwell LLP

(57) ABSTRACT

A prescription handling system that takes filled prescription containers in an automated pharmacy and places them into a package for shipment is described. The handling system includes an inflow to feed containers to a turntable and a robot moves containers from the turntable to a container placement section, which places the containers in a pocket of a package for shipping. Each container for a prescription order is tracked to ensure that only associated containers are packaged together.

28 Claims, 11 Drawing Sheets

SYSTEMS AND METHODS FOR PRESCRIPTION CONTAINER SHIPPING

FIELD

The present application relates generally to the technical field of automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

DETAILED DESCRIPTION

Example systems and methods for a prescription container packaging device (e.g., in a pharmacy) are described.

In the following description, for purposes of explanation, numerous specific details are set forth in order to provide a thorough understanding of example embodiments. It will be evident, however, to one of ordinary skill in the art that embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other prescription containers and packaging having a quantity of a prescription drug contained therein.

The prescription drugs may be dispensed at various sections of the high volume pharmacy. Some prescription orders may require manual fulfillment of order components. Distribution of order components necessitating manual fulfillment is provided by a distribution section and one or more than one manual sections. In general, manual handling includes manual fulfillment of prescription drugs (e.g., by a pharmacist utilizing or directly controlling certain equipment). Manual handling occurs at one or more than one manual sections, from which the order component exits the manual fulfillment device. Some prescription orders or portions of prescription orders may be filled using automated machines, which can fill prescription orders at a greater rate than manual fulfillment.

The prescription drugs may be placed in bottles or containers, e.g., through open tops. The open top of the filled container is then closed, e.g., by a closure device or cap. For example, two different style caps may be used on the container such as a child resistant cap (CRC) cap or an easy-open cap. The cap may be sealed to the container, e.g., by a wrap seal. The seal may at least partially enclose the cap and overlap the container, e.g., adjacent the cap or the open top of the container. In a high volume fulfillment center, automated systems and methods may be used to seal the cap to the container. In some embodiments, a pharmacy order may include multiple different kinds of drugs with each kind retained in separate containers. When appropriate, multiple containers may be shipped together. In general, these containers are grouped together at the end of the filling and then ultimately packaged together for shipping. After grouping the containers are typically placed in a package that may be preloaded with literature relating to the drugs to be shipped therein. The package containing the containers may then be sealed for shipping.

Figure 1:
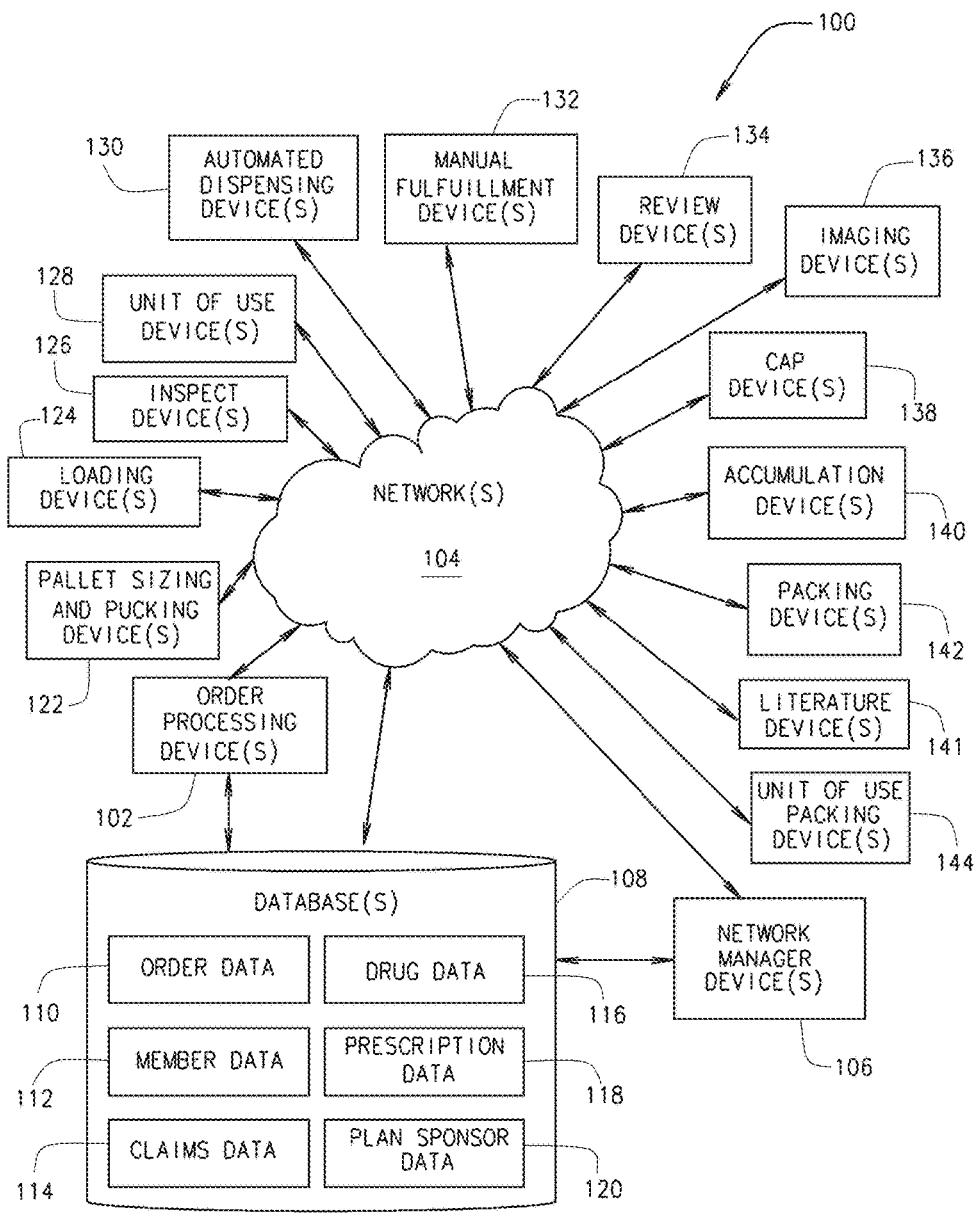
FIG. 1 is a block diagram of an example system, according to an example embodiment.

FIG. 1 is a block diagram of an example system 100, according to an example embodiment. While the system 100 is generally described as being deployed in a high volume pharmacy (e.g., a mail order pharmacy, a direct delivery pharmacy, an automated pharmacy and the like), the system 100 may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together. When the order processing device 102 determines that an order should be consolidated together or multiple containers of an order or associated with a member should be shipped together, the order processing device 102, in some embodiments, also determines the corresponding packaging to be used with shipping. For example, packaging selection by the order processing device 102 may include a four or less container package or an eight or less container package. The package may be sealed after the containers are placed therein by the packing device 142, manually by pharmacy personnel, by a different device, or otherwise.

Examples of the devices 102, 106 include a set-top box (STB), a receiver card, a mobile telephone, a personal digital assistant (PDA), a display device, a portable gaming unit, a tablet, a portable computer and a computing system; however other devices may also be used. For example, the devices 102, 106 may include a mobile electronic device, such an IPHONE or IPAD device by Apple, Inc., mobile electronic devices powered by ANDROID by Google, Inc. and a BLACKBERRY device by Blackberry Limited. The devices 102, 106 may also include other computing devices, such as desktop computing devices, notebook computing devices, netbook computing devices, gaming devices, servers, and the like. The devices 102, 106 may include circuitry, a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no copay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software-as-a-service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of container in which the drug is or is preferably dispensed. In general, prescription materials are a type of order materials that include a tangible electronic copy of information regarding the prescription drug for inclusion with or otherwise in conjunction with the fulfilled prescription. The prescription materials may include tangible electronic information regarding drug interaction warnings, recommended usage, possible side effects, expiration date, date of prescribing, or the like. The electronic information may be stored in a memory, operated on by a processor or otherwise be in a machine readable form. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription container and a closure device or cap) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet and during movement through the fulfillment process. Different pucks may have differently sized and shaped receptacles to accommodate containers of differing sizes, as may be appropriate for different prescriptions. Pucks allow the standardization of equipment engaging differently sized drug containers such that some automated equipment can move the drug container by gripping the puck that is supporting the container and allow the use of a standardized pallet that holds a plurality of pucks have a same outer dimension while having differently sized receptacles therein to hold differently sized drug containers. The pucks may also operate to ensure that a drug container is centered in a location on the pallet.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, a pick and place mechanism, or the like. In one embodiment, the loading device 108 has robotic arms or pickers to grasp a prescription container and move it to and from a pallet. The loading device 124 may also print a label which is appropriate for a container that is to be loaded onto the pallet, and apply the label to the container. The pallet may be located on a conveyor assembly during these operations. In an example embodiment, the drug containers may be positioned in the pucks by the loading device 124 prior to the pucks being placed in the pallet.

The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispensed by other devices in the high volume fulfillment center. Unit of use packaged orders may be combined with other containers for shipment. Such unit of use packages can take the place of a container in a shipment package or placed beneath containers in the shipment package, e.g., before the containers are placed in the package.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100. In an example embodiment, the container may be joined with other containers in a prescription order for a patient or member, e.g., on a pallet or at the accumulation device 140. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station. In some embodiments, at least a portion of the review of a filled prescription container may be performed before the container is capped and sealed. In some embodiments, a portion of the review may occur before the container is packaged for shipment.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise. Such accumulated prescription containers may be packaged together in a shipment package that is then sealed for shipment.

In some embodiments, the literature device 141 folds or otherwise prepares the literature for inclusion with a prescription drug order (e.g., in a shipping container). In some embodiments, the literature device 141 may include a printer system configured to print the literature and an insertion device, which may be separate from the printer system to prepare the literature for inclusion with its associated prescription order. The literature device 141 may build the prescription order by reading the bar codes of the paper as it is presented. Once the literature device 141 builds the correct literature pack associated with the bottle(s) (e.g., by reading bar codes) the literature pack may be folded and placed in sequence with the bottle(s) to be sealed.

The packing device 142 packages a prescription order in preparation for shipping the order, and may be a packaging wrap seal packing device 142. The packaging device 142 may seal a container and package containers for shipment. The packing device 142 may box, bag, or otherwise package the fulfilled prescription order for delivery. The packing device 142 may further place inserts, e.g., literature or other papers, into the packaging received from the literature device 141 or otherwise. For example, bulk prescription orders may be shipped in a box, while other prescription orders may be shipped in a bag which may be a wrap seal bag. In an example embodiment, the packaging may be a substrate configured to receive multiple prescription orders, e.g., containers. The substrate may then be wrap sealed by the container wrap seal packing device 142. The packing device 142 may label the substrate, the box, or the bag with the address and a recipient's name. The label may be printed and affixed to shipping package, e.g., the substrate, the bag or the box, be printed directly onto shipping package, or otherwise associated with the shipping package. The packing device 142 may sort the shipping package for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of containers to be bagged or otherwise packaged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g. by conveyors), networked, and/or otherwise in contact with one another or integrated with one another, e.g., at the high volume fulfillment center. In addition, the functionality of a device may be split among a number of discrete devices and/or combined with other devices.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

Figure 2:
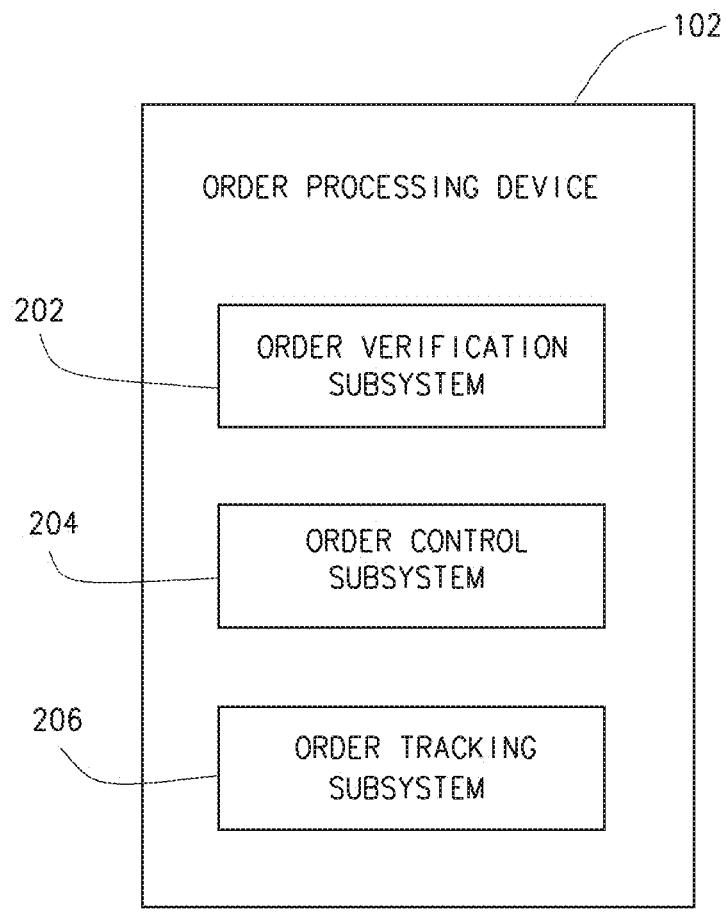
FIG. 2 is a block diagram of an example order processing device that may be deployed within the system of FIG. 1, according to an example embodiment.

FIG. 2 illustrates the order processing device 102, according to an example embodiment. The order processing device 102 may be used by one or more than one operator to generate prescription orders, make routing decisions, make prescription order consolidation decisions, track literature within the system 100, and/or view order status and other order related information. For example, the prescription order may be comprised of multiple order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100.

In some embodiments, the order control subsystem 204 may identify the prescribed drug in one or more than one prescription order as capable of being fulfilled by the automated dispensing device 130. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130.

In some embodiments, the order control subsystem 204 may identify the prescribed drug in one or more than one prescription order as needing to be fulfilled manually and may direct the container or order component to the manual fulfillment device 132 to achieve the manual fulfillment. The order control subsystem 204 may determine which prescriptions are to be launched, and may determine that a pallet of manual-fill containers is to be launched. The order control subsystem 204 may determine that a manual-fill prescription of a specific pharmaceutical is to be launched, and may examine a queue of orders awaiting fulfillment for other prescription orders which will be filled with the same pharmaceutical. The order control subsystem 204 may then launch orders with similar manual-fill pharmaceutical needs together in a pallet to the manual fulfillment device 132. As the devices 122-144 may be interconnected by a system of conveyors or other container movement systems, the order control subsystem 204 may control various conveyors to deliver the pallet from the loading device 124 to the manual fulfillment device 132, for example.

The order tracking subsystem 206 may track a prescription order as it progresses (or stops) toward fulfillment. The order tracking subsystem 206 may track, record and/or update order history, order status, or the like. The order tracking subsystem 206 may store data locally (e.g., in a memory) or as a portion of the order data 110 stored in the database 108. The order tracking subsystem 206 may further track components of a prescription order to ensure that the components arrive at one or more of the packing devices 142, 144 at about the same time.

Figure 3:
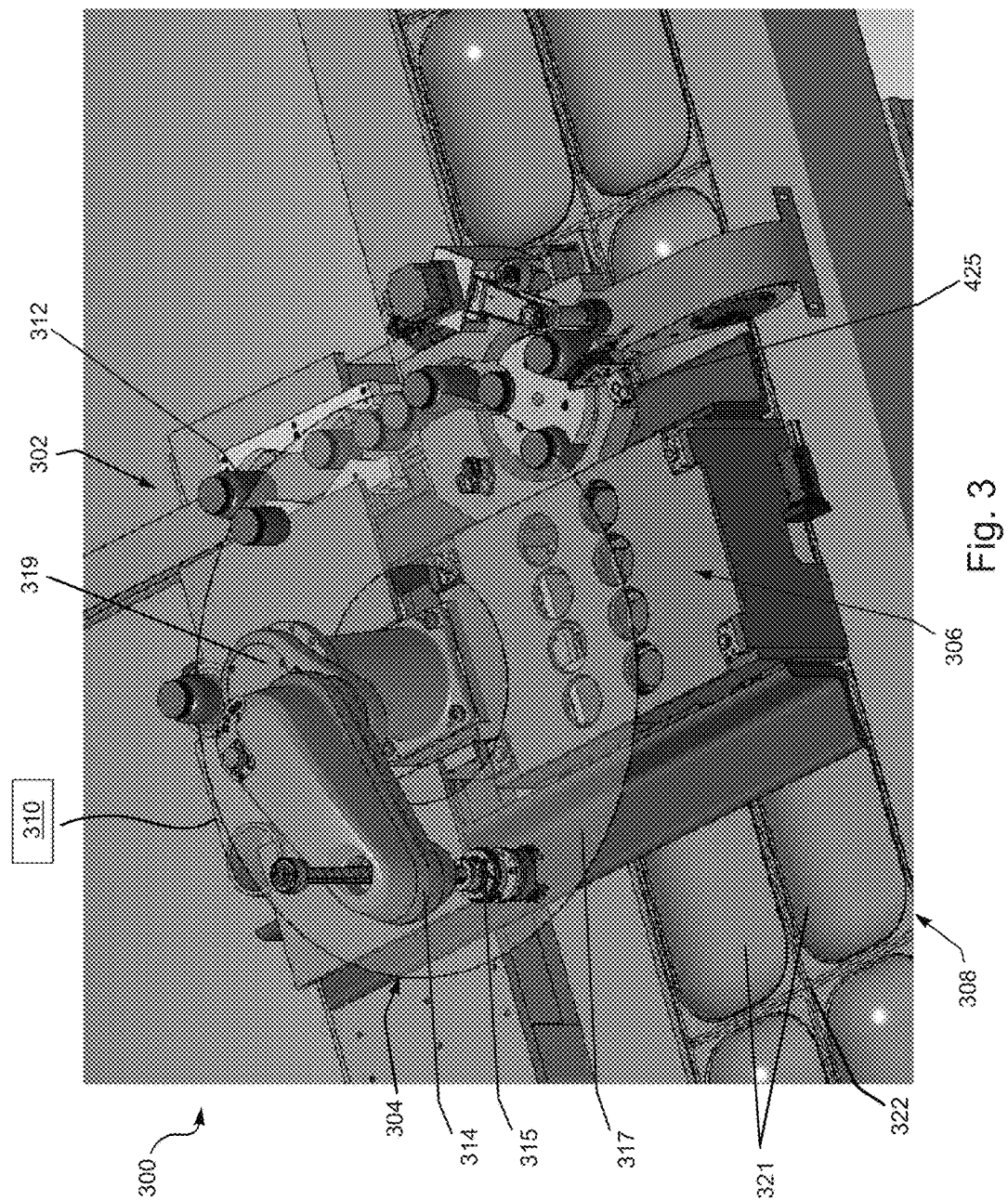
FIG. 3 is a perspective view of a prescription container packaging device that may be deployed within the system of FIG. 1, according to an example embodiment.

FIG. 3 illustrates a prescription package wrap seal device 300, according to an example embodiment. The prescription package wrap seal device 300 may be deployed as a part of the packing device 142, or may be otherwise be deployed in the system 100. The prescription package wrap seal device 300 may include an inflow section 302, a robot section 304, an order placement section 306, a pocket conveyor 308, and a control unit 310. Control unit 310 may operate at the direction of the order processing device 102. Containers 312 may proceed through the prescription package wrap seal device 300 for packing and eventual shipment. A container 312 may represent an order component of a prescription order. One or more than one order component (e.g., multiple containers) may constitute a prescription order. The containers 312 used with the system 100 may include, by way of example, multiple sizes, such as 75 cc, 120 cc, 200 cc, and the like. In some embodiments, multiple sizes of prescription containers may be processed by the system 100.

Robot section 304 may include a robot 314 that may be configured to perform complex movements with the containers 312. The robot 314 may be a SCARA robot or the like. The robot 314 may include a rotatable arm that moves in an XY frame and is fixed in the Z directions. The robot 314 may perform complex movements in three dimensions in some embodiments. The movement of a pickup head 315 may be in an annular travel path 317 radially inwardly toward and outwardly from a base 319 of the robot 314. In an example embodiment, a container 312 may be picked by the robot 314 from the inflow section 302 (within the annular travel path 317), and may be transported to the order placement section 306 (also within the annular travel path 317). The head 315 picks up the container 312 and lowers it into the order placement section 306. In some embodiments, a container 312 may be picked from the inflow section 302 as directed by the order processing device 102 or other processing devices. A single container 312 or multiple containers 312 may be unloaded and distributed from the inflow section 302. The container(s) 312 may be empty and/or uncapped. In some embodiments, the container 312 may be filled, inspected, and otherwise processed at the high volume fulfillment center. Other devices may additional or alternatively be used to pick the container 312, or the container 312 may be manually removed.

The pocket conveyor 308 receives formed pockets from a pocket source. The pocket source is positioned upstream from the order placement section 306. The pocket source may be a thermo, vacuum forming device that takes a roll of stock, e.g., a roll of polymer, and forms it into the pocket with a recess 321 adapted to receive multiple containers 312 along with associated literature. The pocket may also include ledges 322 that may extend around the recess 321 to provide a surface for a seal material to affix thereto to seal the containers in the recess 321. The ledges 322 may also connect to adjacent pockets to each other, here shown in a two-by-two and endless configuration for example. Each pocket may be associated with one prescription order.

Figure 4:
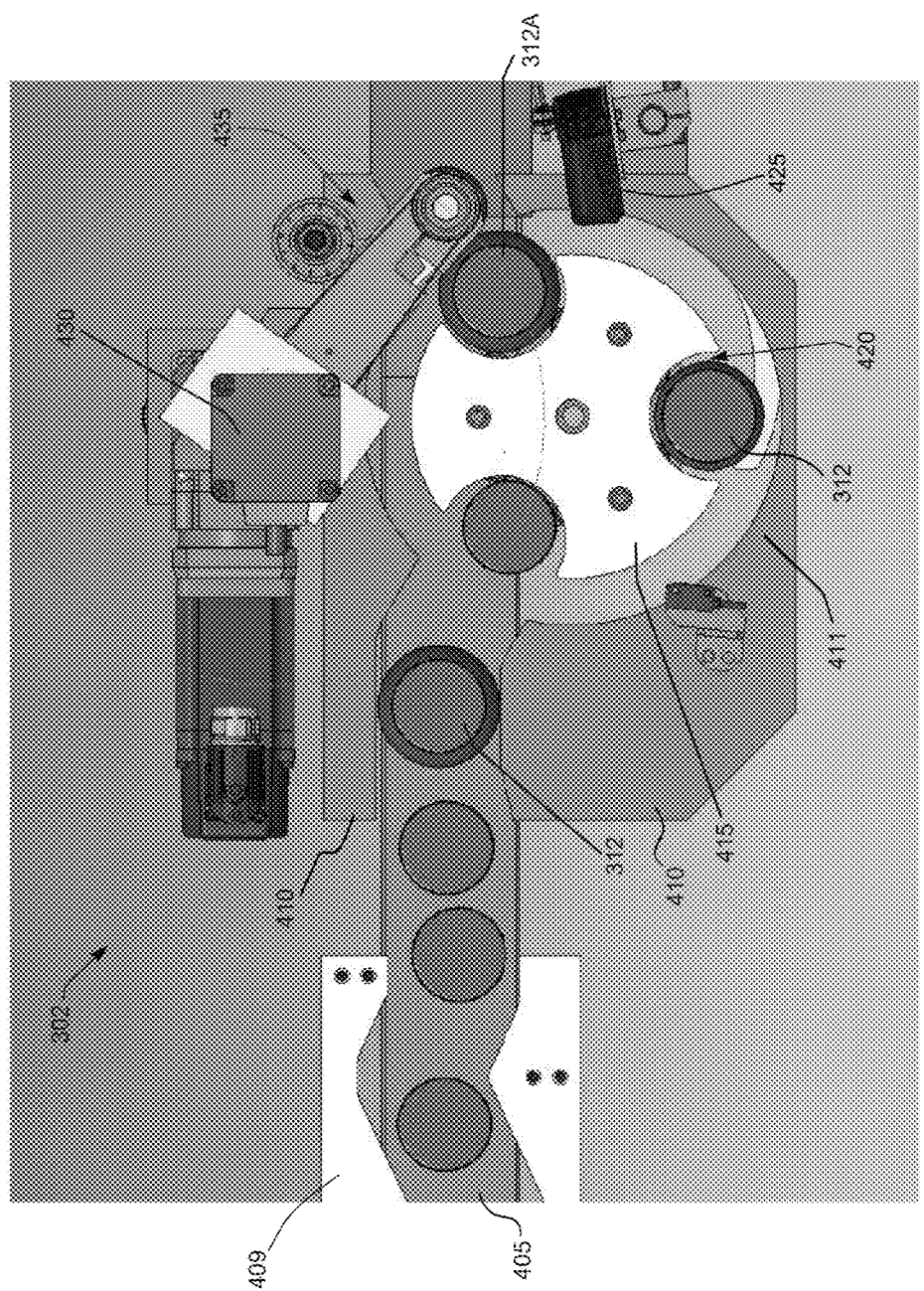
FIG. 4 is a top plan view of an inflow section of the prescription container packaging device of FIG. 3 according to an example embodiment.
Figure 5:
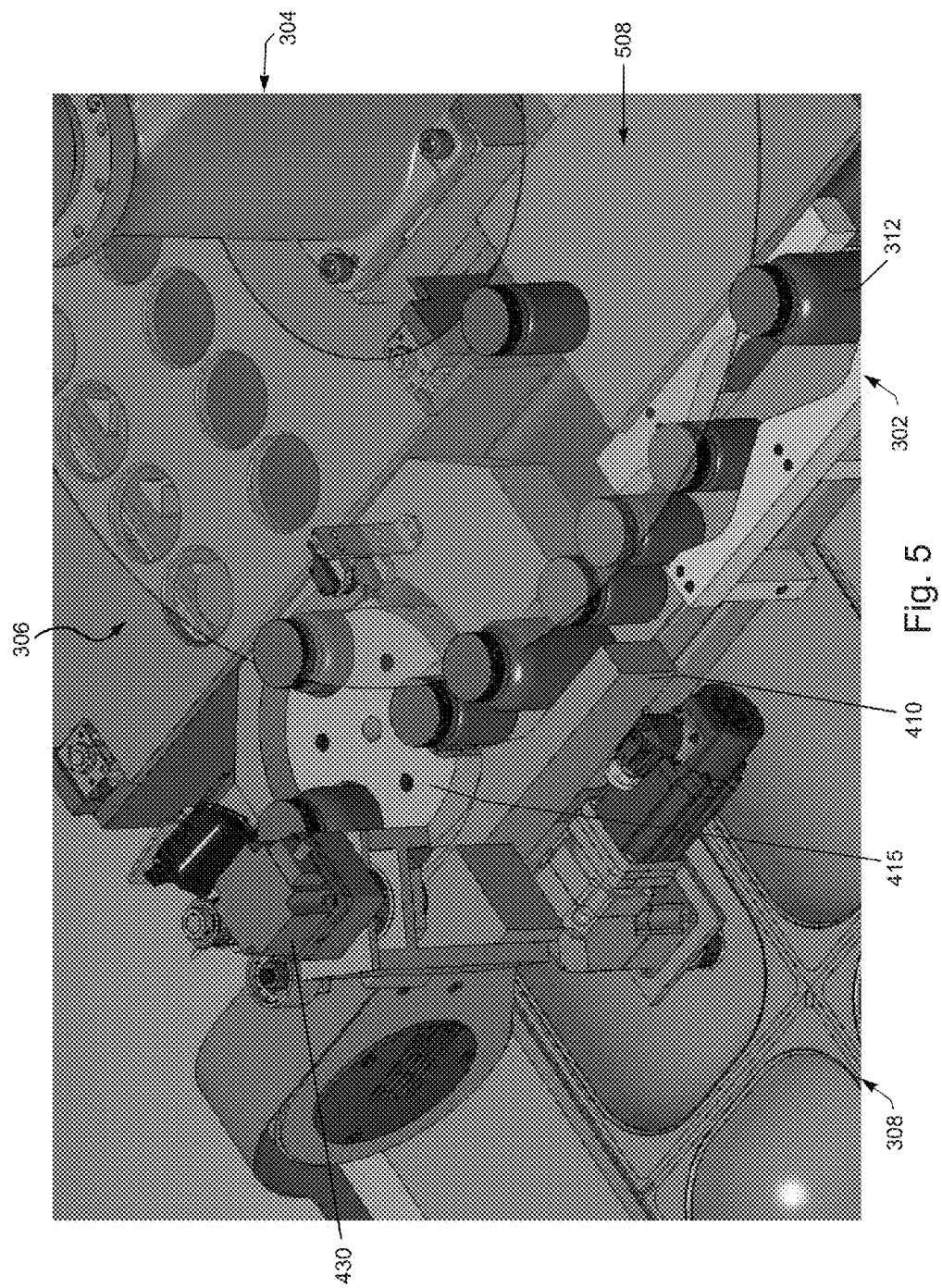
FIG. 5 is a partial perspective view of the prescription container packaging device of FIG. 3 according to an example embodiment.

As shown in FIGS. 4 and 5, the inflow section 302 may include a feed conveyor 405, a first container guide 409, a second container guide 410, a turntable 415 with one or more than one recess 420 therein, a scanner 425, and a motor 430. The feed conveyor 405 may supply containers 312 to the turntable 415, as guided by container guides 409, 410. The first container guide 409 is positioned upstream from the second container guide 410 along the conveyor 405. The first container guide 409 forms an undulating, nonlinear track for the containers 312 being moved by the conveyor 405. The second container guide 410 aligns the containers 312 to the turntable and further reduces the linear alignment of the containers 312 on the conveyor. Moving the containers 312 from a true linear alignment may reduce the pressure on the container at the front of the line adjacent the turntable 415. The nonlinear arrangement of the containers 312 on the conveyor 405 at the inflow section 302 also assists in preventing the labels on the containers from rubbing against each other in the inflow section 302. As a container 312 arrives at the turntable 415, it may enter a recess 420 from an outlet of the second container guide 410, which outlet is at an angle relative to the linear travel direction of the conveyor 405. The second container guide outlet does align with recess 420 of the turntable 415. The turntable 415 supports the container 312 after it moves it off the conveyor 405. The second container guide 410 includes a turntable guide part 411 that extends around the turntable 415 where the containers 312 will travel. The guide part 411 forms a wall adjacent the turntable and may act to prevent a container from exiting the recess 420. As will be understood, the turntable 415 may include a mechanism for supporting a container 312 as it is revolved by the turntable 415 within a recess 420. In an example embodiment, there is a floor beneath the turntable 415 on which the bottom of the container 312 rests. The sides of the recess 420 may contact the container 312 and move it non-linearly. In another example embodiment, the recess 420 may include gripper arms that can hold the container 312 in the recess. The container 312 may rotate around turntable 415 within its recess 420, and travel past a scanner 425. The scanner 425 scans the container 312. The scanner 425 may include an image sensor that captures an image of the container 312 with the label and/or a barcode scanner. A motor, e.g., motor 430, may drive rotation of the turntable 415.

A container rotating mechanism 435 may move into engagement with a container 312A to rotate (e.g., spins in the recess 420) the container 312A such that the label, barcode, QR code, or other identifying information is visible to the scanner 425. The container rotating mechanism 435 may include a drive wheel, a drive belt, or the like that is brought into engagement with the container 312A. A motor, e.g., a stepper motor, of the container rotating mechanism 435 may drive the drive wheel or drive belt to rotate the container 312. The recess 420 of the turntable 415 may include bearings or free wheels to allow the container 312A to spin under force from the container rotating mechanism 435. The free wheels in the recess 420 allow the container to rotate without damaging the label on the container 312A.

As best shown in FIG. 5, turntable 415 revolves a container 312 from the feed conveyor 405 of the inflow section 302 toward the robot section 304, such that the robot 314 may pick the container 312 from the turntable 415. The robot 314 may pick the container 312 after it has been identified by the scanner and other devices.

Figure 6:
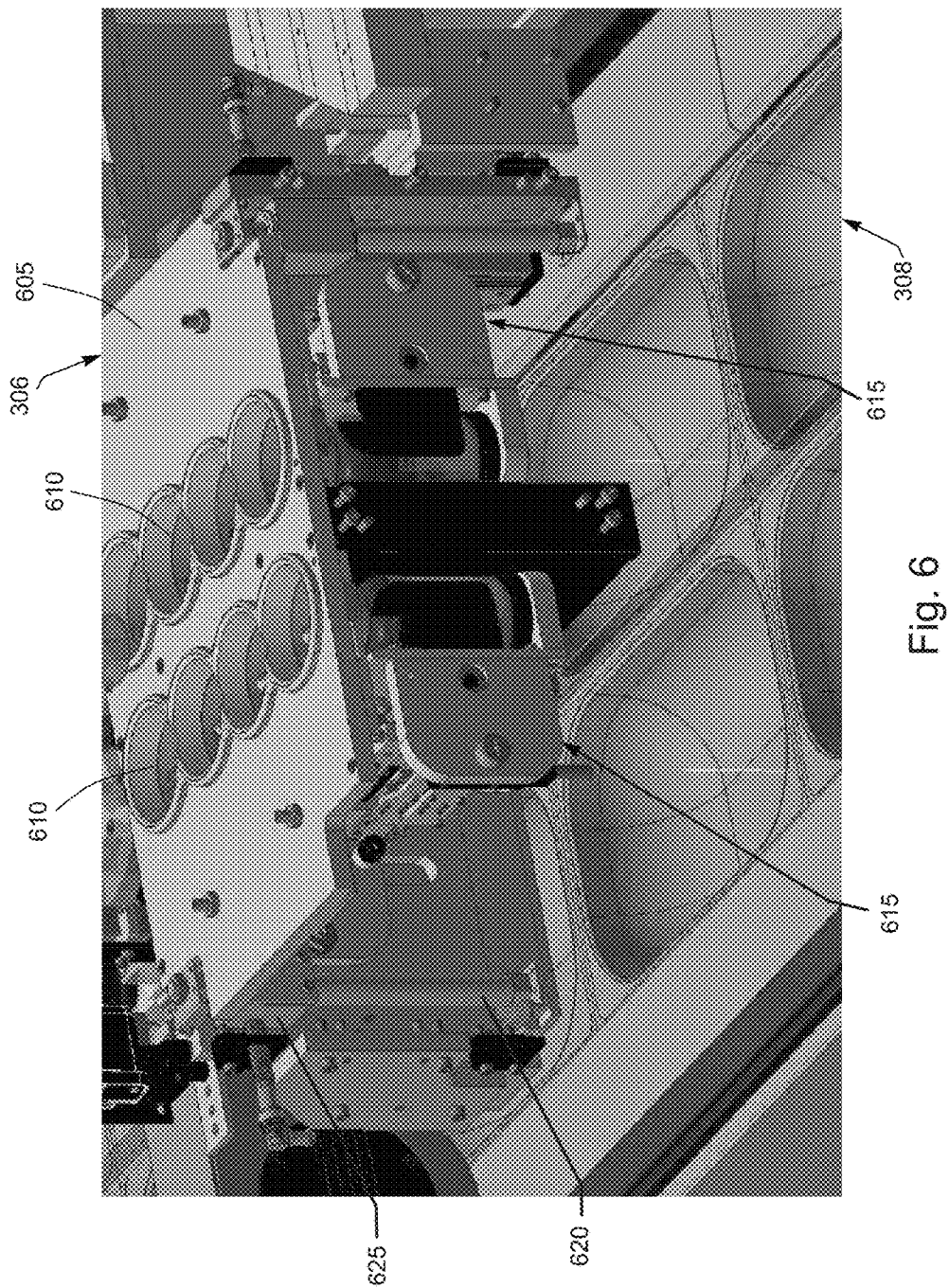
FIG. 6 is a perspective view of an order placement section of the prescription container packaging device of FIG. 3 in a raised position, according to an example embodiment.
Figure 8:
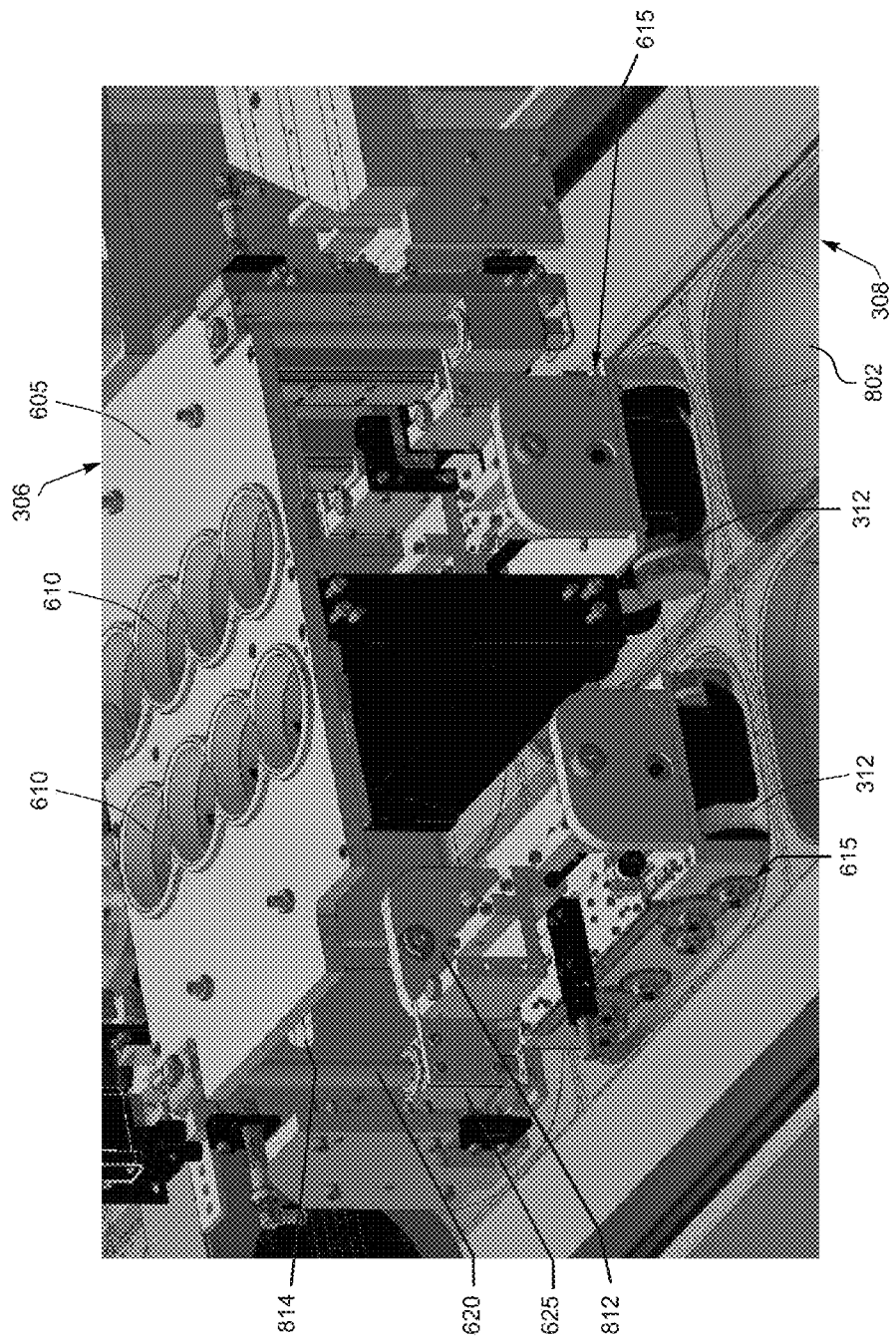
FIG. 8 is a perspective view of the order placement section of FIG. 6 in a lowered position, according to an example embodiment.

Once the robot 314 has picked the container 312 from the turntable 415, it may then move the container 312 to the order placement section 306. The order placement section 306 may also include a storage area 508 whereat the robot 314 can place a container 312 when it is not placing that container 312 in the order placement section 306. The systems and methods controlling the robot 314 may determine that a specific container 312 should not be placed into the order placement section 306. Examples may include that the container 312 does not belong to a specific order being packed, the container was not verified by the image taken by the scanner, and the like. As best shown in FIGS. 6 and 8, the order placement section 306 may include a plate 605 with one or more than one slots 610 extending therethrough. The slots 610 may be multiple apertures to guide containers from the robot 314 to a carriage rack positioned below the plate 605. One, or more than one, carriage rack 615 may be positioned beneath plate 605. The order placement section 306 may also include a guide rod 620 along which a slide 625 may travel. The slide 625 may be connected to a carriage rack 615, thereby allowing the carriage rack 615 to similarly travel along the guide rod 620. As shown in FIG. 6, a carriage rack 615 may be positioned in a raised position such that it can receive containers 312 from the robot 314 through the slots 610. In the raised position, the slide 625 is visible at the top of the guide rod 620.

Figure 7:
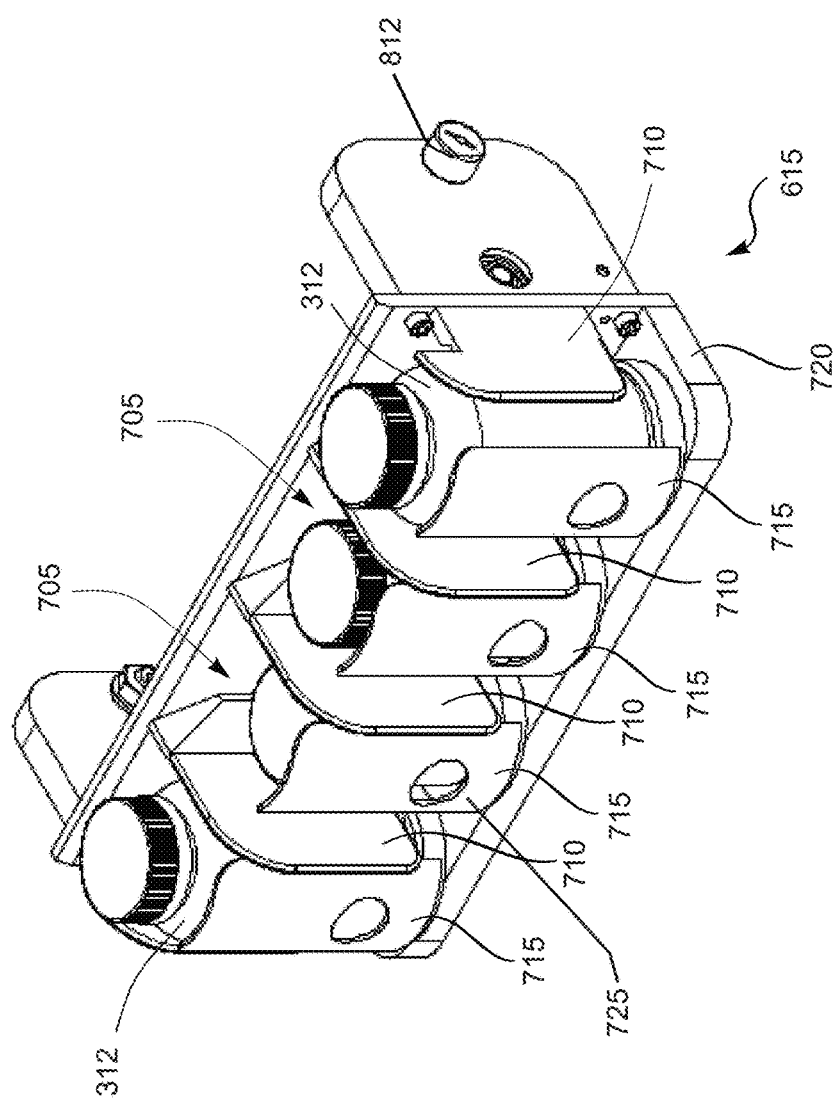
FIG. 7 is a perspective view of a carriage rack of the order placement section of FIG. 6.

As shown in FIGS. 6 and 8, the plate 605 includes eight total slots 610 positioned overtop of two carriage racks 615, with four slots 610 positioned over each respective carriage rack 615. FIG. 7 illustrates an example embodiment of a carriage rack 615 in more detail. A carriage rack 615 may include one or more than one receptacle 705, each for receiving a container 312 therein. The number of receptacles 705 in a carriage rack 615 may correspond to the number of slots 610—or a portion of the slots 610—in the plate 605, for receiving containers 312 therethrough. A carriage rack 615 may also include one or more than one divider 710 for separating receptacles 705 from one another. Each receptacle 705 may also include a release gate 715, as well as a floor 720. Each of the release gates 715 may include an aperture 725 therein. The aperture 725 allows a sensor access to the interior of the receptacle 705. Such a sensor may determine if a container 312 is present within the receptacle 705. If the present methods and systems determine that a particular container 312 should be in the receptacle but the sensor does not sense that the container 312 is present, the methods and systems will flag this prescription order as a potentially erroneous fill as a component may be missing. This prescription order in the carriage may still be placed in the pocket, as will be explained in greater detail herein, but not released from the high volume pharmacy. Such a prescription order may be sent for further manual inspection.

As shown in FIG. 8, the slide 625 may move downwardly along guide rod 620, thereby moving the carriage rack 615 into a lowered position above pocket conveyor 308. In the lowered position, the carriage rack 615 may also rotate so that containers 312 are selectively retained within the respective receptacles 705 by the release gates 715. e.g., with the release gates being positioned between the containers in the receptacle 705 and the surface of the pocket 802. Such rotation may be approximately ninety degrees, but this may be altered as desired in order properly position the containers within and/or above a pocket 802 of the pocket conveyor 308. By lowering and rotating the carriage rack 615 to a position immediately above and/or within a pocket 802, the containers 312 in the carriage rack 615 are now positioned on their side, e.g., with the top of the container 312 being positioned toward the center of the endless stream of pockets 802. The carriage rack 615 may move the gates 715 to position the containers 312 in the carriage rack into the pocket 802 by selectively opening the release gates 715. The carriage being positioned in the pocket 802 will result in a low drop into the pocket. Such selective actuation of one or more than one of the release gates may be achieved by any mechanism by an actuator that is controlled by the control devices described herein. This results in a lower chance for any container 312 to bounce out of or otherwise miss its intended pocket 802, or being damaged while being inserted. The carriage rack(s) 615 may then be counter-rotated and lifted back to the raised position shown in FIG. 6 for refilling with the release gates being closed after the carriage rack 615 is raised out of the pocket 802.

The carriage 615 may have a pin 812 that is mated to a guide path 814. While the carriage 615 moves along the slide 620 from the raised position to the lowered position, the pin 812 is in a horizontal part to hold the carriage 615 in the upper non-rotated position directly beneath plate 605. The pin 812 moves along the path 814 and turns inwardly to cause the carriage 615 to pivot to the side. When the prescription order includes literature, the literature may be placed in the bottom of the pocket 802 before the carriage places the containers 312 associated with the order in the pocket. This may occur before the pocket arrives at the container packaging as described herein. The carriage 615 places the containers on top of the literature in the pocket. Thereafter, the pocket may travel to a sealing device that seals the open top of the pocket to secure the container, and literature, if any, in the pocket for shipment.

Figure 9:
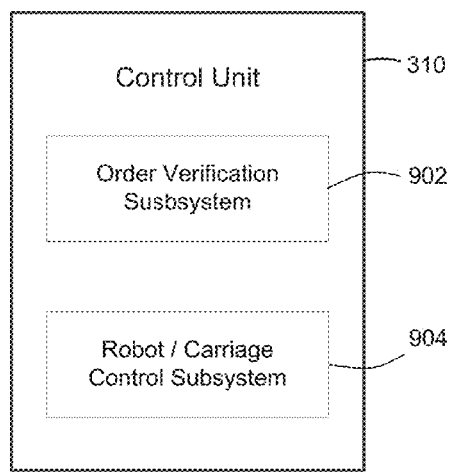
FIG. 9 is a block diagram of a control unit that may be deployed within the prescription container packaging device of FIG. 3, according to an example embodiment.

FIG. 9 illustrates the control unit 310, according to an example embodiment. The control unit 310 may be deployed in packing device 142, or may otherwise be used.

The control unit 310 may be responsible for directing the robot 314 to place the containers 312 picked from the turntable 415 into a carriage rack 615. The control unit 310 may be communicatively connected to one or more than one component in the inflow section 302, the order placement section 306, and/or the pocket conveyor 308. The control unit 310 may include an order verification subsystem 902 and a robot/carriage control subsystem 904. The order verification subsystem 902 may enable the control unit 310 to verify that the correct containers 312 have been fed to the turntable 615 and/or picked by the robot 314 and/or placed into a carriage rack 615. Further, the order verification subsystem 902 may confirm that all desired containers 312 have been placed within a carriage rack 615 for further placement within a pocket 802. The robot/carriage control subsystem 504 may enable the control unit 310 to control the robot 314 and carriage rack 615.

Figure 10:
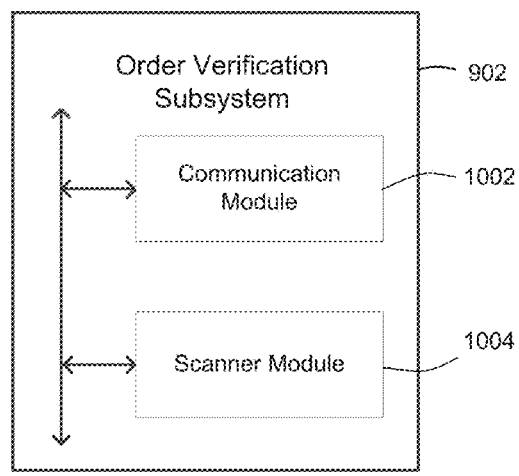
FIG. 10 is a block diagram of an order verification subsystem that may be deployed within the control unit of FIG. 9, according to an example embodiment.

FIG. 10 illustrates an example order verification subsystem 902 that may be deployed in the control unit 310, or may be otherwise deployed in another system. One or more modules are communicatively coupled and included in the order verification subsystem 902 to enable the order verification subsystem 902 to identify and monitor the progress of containers 312 through the prescription package wrap seal device 300. The modules of the order verification subsystem 902 that may be included are a communication module 1002 and/or a scanner module 1004. Other modules may also be included.

In some embodiments, the modules of the order verification subsystem 902 may be distributed so that some of the modules are deployed in other devices within the pharmacy. In one embodiment, the modules are deployed in memory and executed by a processor coupled to the memory. The functionality contained within the modules 1002, 1004 may be combined into a lesser number of modules, further divided among a greater number of modules, or redistributed among existing modules. Other configurations including the functionality of the modules 1002, 1004 may be used.

The communication module 1002 may manage communication with, for example, database(s) 108 to access one or more than one of order data 110, member data 112, claims data 114, drug data 116, prescription data 118, and plan sponsor data 120 in order to determine which container or containers form a prescription order. Where the control unit 310 is a part of the order processing device 102, a distinct communication module 1002 may be omitted. The scanner module 1002 may be in communication with scanner 425 in order to identify containers 312 at the turntable 415.

Figure 11:
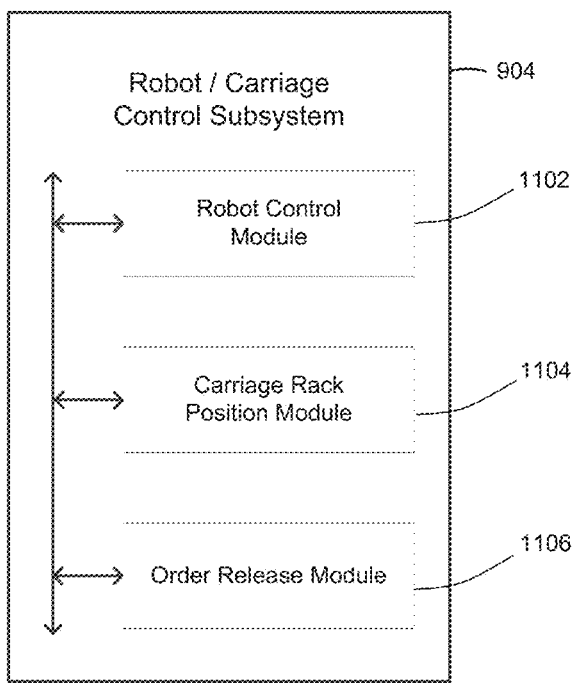
FIG. 11 is a block diagram of a robot/carriage control subsystem that may be deployed within the control unit of FIG. 9, according to an example embodiment.

FIG. 11 illustrates an example robot/carriage control subsystem 904 that may be deployed in the control unit 302, or may be otherwise deployed in another system. One or more modules are communicatively coupled and included in the robot/carriage control subsystem 904. The modules of the robot/carriage control subsystem 904 that may be included are a robot control module 1102, a carriage rack position module 1104, and an order release module 1106. Other modules may also be included.

In some embodiments, the modules of the robot/carriage control subsystem 904 may be distributed so that some of the modules are deployed in other devices within the pharmacy. In one embodiment, the modules are deployed in memory and executed by a processor coupled to the memory. The functionality contained within the modules 1102-1106 may be combined into a lesser number of modules, further divided among a greater number of modules, or redistributed among existing modules. Other configurations including the functionality of the modules 1102-1108 may be used.

The robot control module 1102 may be in communication with the robot 314, and may control when and where the robot 314 picks a container 312 from the turntable 415. The robot control module 1102 may also determine which slot 610 and receptacle 705 the container 312 is placed by the robot 315, based on information obtained by the communication module 1002 regarding the prescription order with which a given container 312 is associate. The carriage rack position module 1104 may be in communication with carriage rack(s) 615. Thereby, the carriage rack position module 1104 may control whether each such carriage rack 615 moves to its raised position to receive one or more than one container 312, or to its lowered position for preparing to place one or more than one container 312 into a pocket 802. The order release module 1106 may be in communication with release gates 715. The order release module 1106 may cause the selective actuation of release gates 715 to allow placement of one or more containers into a pocket 802 from respective receptacles 705.

Figure 12:
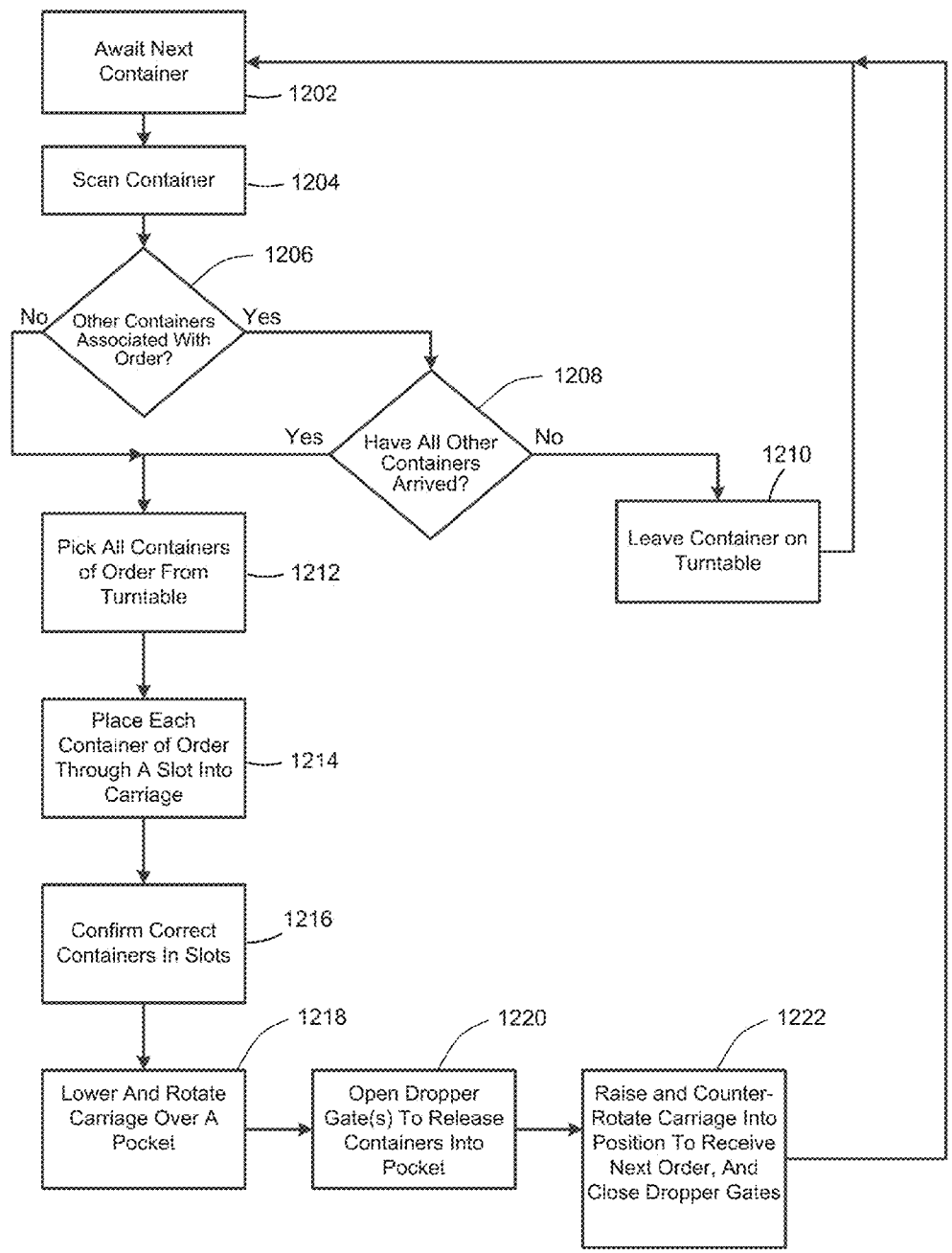
FIG. 12 is an example process flow illustrating a container packaging method, according to an example embodiment.

FIG. 12 illustrates a prescription package wrap seal method 1200, according to an example embodiment. The method 1200 may be performed by prescription package wrap seal device 300 as instructed by control unit 302, or may be otherwise performed.

At block 1202, the device 300 awaits the next container 312. At block 1204, a container 312 arrives at the turntable 415 and is scanned by scanner 425. At decision point 1206, the communications module 1002 accesses various data in database(s) 108 and determines whether there are additional containers 312 included in the order associated with the scanned container 312. If not, the method 1200 advances to block 1212 as discussed in detail below. However, where there are additional containers associated with the current order, the method 1200 advances to decision point 1208 where a determination is made as to whether all containers 312 in the current order have arrived at the device 300. If so, the method 1200 again advances to block 1212 discussed below. However, where additional containers 312 have yet to arrive at the device 300, the scanned container remains in the turntable 415 at block 1210 and the method 1200 reverts to block 1202 to await the next container 312. It is noted that a container 312 associated with an order for which not all containers 312 have arrived at the device 300 may be otherwise dealt with. As a non-limiting example, such a container 312 may be moved to a holding area 508, or may be placed into the carriage rack 615 as discussed in detail below to await further containers 312 in the order.

If, at block 1208 it is determined that all containers 312 have arrived at the device 300, the method 1200 advances to block 1212 where the container 312 is picked from the turntable 415 by robot 314. At block 1214, the container 312 and any selected containers 312 may be placed through a slot 610 into a receptacle 705 of the carriage rack 615. At block 1216, the containers in the carriage rack 615 may again be confirmed by one or more additional scanners, e.g., light sensors, RF sensors, optical sensors, and the like. At block 1218, one or more than one carriage rack 615 may be moved to its lowered position, and may be rotated into position above a pocket 802. At block 1220, one or more than one release gate 710 may be actuated, thereby opening the release gate 710 to place the one or more than one container 312 into the pocket 802. At block 1222, the one or more carriage rack 615 may be moved and counter-rotated into its raised position for future refilling. The method 1200 then reverts back to block 1202.

Figure 13:
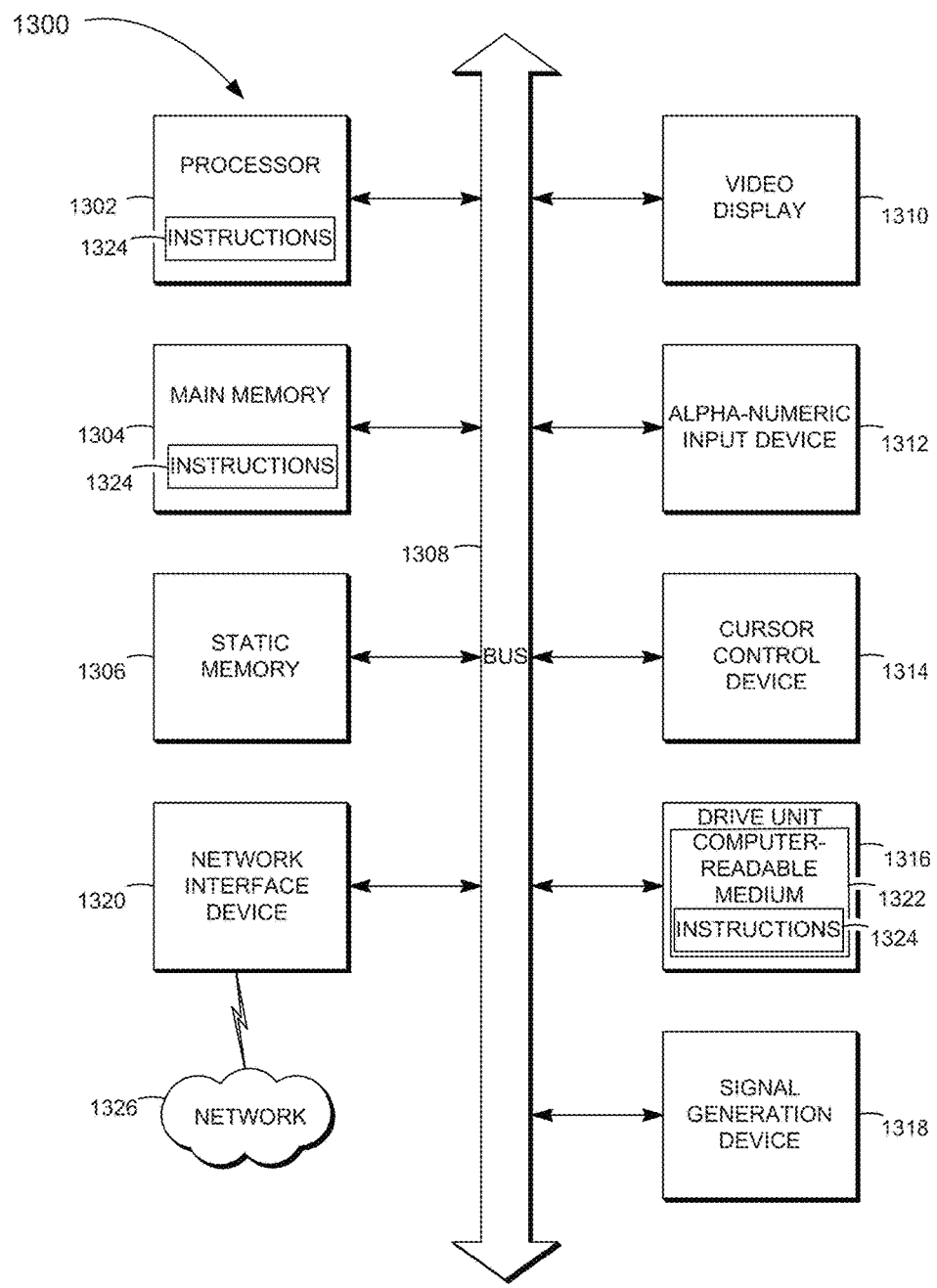
FIG. 13 is a block diagram of a machine in the example form of a computer system within which a set of instructions for causing the machine to perform any one or more of the methodologies discussed herein may be executed or stored.

FIG. 13 shows a block diagram of a machine in the example form of a computer system 1300 within which a set of instructions may be executed causing the machine to perform any one or more of the methods, processes, operations, or methodologies discussed herein. The device 102, 106, 122-144, for example, may include the functionality of the one or more computer systems 1300.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1300 includes a processor 1302 (e.g., a central processing unit (CPU) a graphics processing unit (GPU) or both), a main memory 1304 and a static memory 1306, which communicate with each other via a bus 1308. The computer system 1300 further includes a video display unit 1310 (e.g., a liquid crystal display (LCD) or a cathode ray tube (CRT)). The computer system 1300 also includes an alphanumeric input device 1312 (e.g., a keyboard), a cursor control device 1314 (e.g., a mouse), a drive unit 1316, a signal generation device 1318 (e.g., a speaker) and a network interface device 1320.

The drive unit 1316 includes a computer-readable medium 1322 on which is stored one or more sets of instructions (e.g., software 1324) embodying any one or more of the methodologies or functions described herein. The software 1324 may also reside, completely or at least partially, within the main memory 1304 and/or within the processor 1302 during execution thereof by the computer system 1300, the main memory 1304 and the processor 1302 also constituting computer-readable media.

The software 1324 may further be transmitted or received over a network 1326 via the network interface device 1320.

While the computer-readable medium 1322 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium. The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In some embodiments, a system may comprise an inflow section configured to supply filled prescription containers. Additionally, a robot may be provided for picking a container from the inflow section. A container placement section may include a carriage rack, which itself includes a receptacle sized to receive a container therein from the robot, as well as a selectively openable release gate associated with the receptacle. The carriage rack may include a raised position oriented to vertically receive the container within a receptacle from the robot and a lowered position oriented to horizontally place the container in a pocket. In the lowered position, the release gate is positioned to release the container from the receptacle of the carriage rack into the pocket.

In some embodiments, a method may comprise the step of scanning at least one container via a scanner. Further, a prescription order may be identified via a processor, and the prescription order may be associated with the at least one container based on the scan and stored order information. The processor may then determine whether all desired containers associated with the prescription order are available for packing based on the stored order information and the scan. The desired containers may be placed into respective receptacles of a carriage rack while the carriage rack is in a raised position, and the carriage rack may be moved from the raised position to a lowered position. At least one release gate may then be actuated to place the desired containers into a pocket.

The present disclosure makes reference to a robot and words of similar import. A robot can be a machine capable of carrying out a complex series of actions automatically. These complex series of actions may include picking up, orientating, positioning and/or releasing a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, e.g., a robot may move location, have an articulated arm, have grasping structures that replicate like fingers and do not damage containers, and the like.

Thus, prescription package wrap seal methods and systems have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A system comprising:
    an inflow section configured to supply filled prescription containers;
    a robot for picking a container from the inflow section; and
    a container placement section including a carriage rack, the carriage rack including a receptacle sized to receive the container therein from the robot and a selectively openable release gate associated with the receptacle,
    wherein the carriage rack has a raised position oriented to vertically receive the container within the receptacle from the robot and a lowered position oriented to horizontally place the container in a pocket; and
    wherein in the lowered position, the release gate is positioned to release the container from the receptacle of the carriage rack into the pocket.

2. The system of claim 1, wherein the inflow section further comprises:
    a feed conveyor;
    a turntable; and
    a scanner;
    wherein said scanner is positioned to scan the container with the container in the turntable and the robot is positioned to pick the container from the turntable.

3. The system of claim 2, wherein the inflow section further comprises:
    a container guide positioned to direct the container into and around the turntable, the container guide being configured to disrupt linear alignment of the containers on the feed conveyor.

4. The system of claim 2, wherein the turntable includes a recess sized to receive the container therein.

5. The system of claim 1, further comprising:
a slide connected to the carriage rack, the slide being positioned to slide along a guide rail to move the carriage rack between the raised and lowered positions.

6. The system of claim 1, wherein a first orientation of the carriage rack in the raised position is approximately ninety degrees offset from a second orientation of the lowered position.

7. The system of claim 1, wherein the carriage rack in the lowered position is oriented with at least one release gate oriented generally parallel to the pocket.

8. The system of claim 1, wherein the carriage rack in the lowered position is oriented such that selective actuation of the release gate causes a container in the receptacle associated with the release gate to release from the receptacle into the pocket.

9. The system of claim 1, wherein the pocket is associated with a pocket conveyor.

10. The system of claim 1, wherein the lowered position of the carriage rack is at least one of: at least partially within the pocket and immediately proximate the pocket.

11. The system of claim 1, further comprising:
a processor,
wherein the processor controls the robot and carriage rack, and determines placement of at least one container within the carriage rack.

12. The system of claim 11, further comprising:
a processor,
wherein the processor controls the movement of the carriage rack between the raised and lowered positions, and controls the selective actuation of the release gate.

13. The system of claim 1, wherein the carriage rack further includes a plate having at least one slot therethrough, the number of slots corresponding to a number of receptacles.

14. The system of claim 13, wherein each slot is positioned overtop of and vertically aligned with a respective receptacle when the carriage rack is in the raised position.

15. A method comprising:
picking, by a robot, a container from an inflow section;
placing, by the robot, the container in a carriage rack when the carriage rack is in a raised position, the carriage rack including a receptacle sized to receive the container therein from the robot; and
releasing, by a selectively openable release gate associated with the receptacle, the container from the receptacle of the carriage rack into the pocket when the carriage rack is in a lowered position,
wherein the raised position of the carriage rack is oriented to vertically receive the container within the receptacle from the robot, and
wherein the lowered position of the carriage rack is oriented to horizontally place the container in a pocket.

16. The method of claim 15, further comprising:
scanning, by a scanner, the container when the container is in a turntable of the inflow section,
wherein the robot picks the container from the turntable.

17. The method of claim 16, further comprising:
directing, by a container guide, the container into and around the turntable; and
disrupting, by the container guide, linear alignment of the container on a feed conveyor of the inflow section.

18. The method of claim 16, further comprising:
receiving, by the turntable, the container in a recess sized to receive the container.

19. The method of claim 15, further comprising:
sliding, by a slide connected to the carriage rack, along a guide rail; and
moving, by the slide, the carriage rack between the raised and lowered positions.

20. The method of claim 15, wherein moving the carriage rack to the raised position causes a first orientation of the carriage rack to be approximately ninety degrees offset from a second orientation of the lowered position.

21. The method of claim 15, wherein moving the carriage rack to its lowered position orients the carriage rack such that the release gate is oriented generally parallel to the pocket.

22. The method of claim 15, wherein moving the carriage rack to its lowered position orients the carriage rack such that selective actuation of the release gate causes the container in the receptacle associated with the release gate to release from the receptacle into the pocket.

23. The method of claim 15, further comprising associating the pocket with a pocket conveyor.

24. The method of claim 15, wherein moving the carriage rack to the lowered position causes the carriage rack to be at least partially within the pocket or immediately proximate the pocket.

25. The method of claim 15, further comprising:
controlling, by a processor, the robot and carriage rack; and
determining, by the processor, placement of the container within the carriage rack.

26. The method of claim 25, further comprising:
controlling, by a processor, movement of the carriage rack between the raised and lowered positions; and
controlling, by the processor, the selective actuation of the release gate.

27. The method of claim 15, wherein the carriage rack further includes a plate having at least one slot therethrough, the number of slots corresponding to a number of receptacles.

28. The method of claim 27, further comprising positioning each slot overtop of and vertically aligned with a respective receptacle when the carriage rack is in its raised position.

* * * * *